United States Patent
Igaki

(12) United States Patent    (10) Patent No.: US 7,066,952 B2
Igaki    (45) Date of Patent: Jun. 27, 2006

(54) METHOD FOR MANUFACTURING YARN FOR VESSEL STENT

(75) Inventor: Keiji Igaki, Kyoto (JP)

(73) Assignee: Kabushikikaisha Igaki Iryo Sekkei, Kyoto (JP)

( * ) Notice: Subject to any disclaimer, the term of this patent is extended or adjusted under 35 U.S.C. 154(b) by 0 days.

(21) Appl. No.: 10/283,101

(22) Filed: Oct. 30, 2002

(65) Prior Publication Data

US 2003/0055488 A1    Mar. 20, 2003

Related U.S. Application Data

(63) Continuation of application No. 09/530,986, filed as application No. PCT/JP99/04884 on Sep. 8, 1999, now Pat. No. 6,500,204.

(51) Int. Cl.
*A61F 2/06*    (2006.01)

(52) U.S. Cl. ..................... 623/1.15; 623/1.18

(58) Field of Classification Search ........ 623/1.1–1.23; 606/108, 191–198; 600/1–8
See application file for complete search history.

(56) References Cited

U.S. PATENT DOCUMENTS

| | | | | |
|---|---|---|---|---|
| 5,160,341 A | * | 11/1992 | Brenneman et al. | ........ 606/198 |
| 5,762,625 A | | 6/1998 | Igaki | |
| 5,763,098 A | * | 6/1998 | Kameoka et al. | ........... 428/481 |
| 6,053,940 A | | 4/2000 | Wijay | |

* cited by examiner

*Primary Examiner*—Vy Q. Bui
(74) *Attorney, Agent, or Firm*—Rader, Fishman & Grauer PLLC

(57) ABSTRACT

A stent for a vessel implanted in the vessel of the living body including a main body portion of the stent formed into a tube by a yarn formed of a biodegradable polymer exhibiting a shape memory function. The main body portion of the stent is shape-memorized to a size that can be inplanted in the vessel. The main body portion of the stent is implanted in the vessel of the living body as it is contracted in diameter by an external force, and is enlarged in diameter by being heated with the temperature of the living body. The main body portion of the stent is formed by winding a yarn formed of a biodegradable polymer in a tube form as the yarn is bent in a zigzag design. The main body portion of the stent is enlarged or contracted in diameter with the bends of the yarn as the displacing portions.

18 Claims, 4 Drawing Sheets

METHOD FOR MANUFACTURING YARN FOR VESSEL STENT

This application is a continuation of U.S. application Ser. No. 09/530,986 now U.S. Pat. No. 6,500,204 which was the National Stage of International Application No. PCT/JP99/04884, filed Sep. 8, 1999.

TECHNICAL FIELD

This invention relates to a stent for the vessel mounted in the vessel, such as blood vessel, lymphatic vessel, bile duct or urinary duct to maintain a constant state in the lumen of the vessel.

BACKGROUND ART

Heretofore, if a stenosis portion has occurred in the vessel of a living body, in particular the blood vessel, such as artery, a balloon forming portion provided in the vicinity of the distal end of the balloon catheter is inserted into this stenosis portion. This balloon forming portion is expanded to form a balloon to expand the stenosis portion of the blood vessel to improve the blood flow, by way of the transcutaneous blood vessel forming technique (PTA).

It has been clarified that, if the PTA is applied, stenosis tends to be produced at a high probability in the once stenosis portion.

In order to prevent this restenosis, the current practice is to apply a tubular stent in the site processed with the PTA. This stent is inserted into the blood vessel in a diameter-contracted state and subsequently implanted in the blood vessel as it is expanded in diameter to support the blood vessel from its inside to prevent restenosis from being produced in the blood vessel.

As this sort of the stent, there have so far been proposed a balloon expanding stent and a self-expanding stent.

The balloon expanding stent is applied over a balloon provided in a folded and diameter-contracted state in a catheter and, after being inserted in the targeted site for implantation, such as a site of lesion, where the blood vessel is stenosis, the balloon is expanded and increased in diameter to support the inner surface of the blood vessel. Once expanded in diameter, the balloon expanding stent is fixed in this expanded state and cannot be deformed in keeping with the pulsations of the blood vessel wall. On the other hand, if the balloon expanding stent is deformed after being expanded in diameter and implanted in this condition in the blood vessel, it cannot be restored to its original expanded state, such that there is the risk that the stent cannot support the inner surface of the blood vessel reliably.

The self-expanding stent is housed in the diameter-contracted state in a holder, such as a tube, having an outer diameter smaller than the inner diameter of the targeted site for implantation in the blood vessel, and is inserted in the targeted site for implantation in the blood vessel as it is housed in a holder. The stent, thus inserted in the targeted site for implantation in the blood vessel, is extruded or extracted from the holder so as to be expanded in diameter to the pre-contracted state, by exploiting the force of restoration proper to the stent, thus continuing to support the inner wall of the blood vessel.

As this sort of the self-expanding stent, there is proposed such a one obtained on warping a linear member of metal, such as stainless steel, into a sinusoidal or zig-zag design, to form a tube.

With the self-expanding stent formed from a metal linear member, the outer diameter prevailing at the time of expansion is difficult to control precisely, such that the stent is likely to be expanded excessively in comparison with the inner diameter of the blood vessel in which it is implanted. Moreover, if the force of holding the stent in the contracted state is removed, the stent is expanded abruptly. If the stent inserted into the blood vessel is expanded abruptly, the inner wall of the blood vessel is likely to be injured.

As the self-expanding stent, those formed of shape memory alloys, such as T—Ni, Ti—Ni—Cu or Ti—Ni—Fe based alloys, have been proposed.

The stent, formed of shape memory alloys, is kept to its size when it is implanted in the targeted loading site in the blood vessel, by the shape memory action, and is subsequently contracted in diameter, so as to be inserted in this diameter-contracted state in the blood vessel. After insertion into the targeted loading site in the blood vessel, this stent is expanded to the size of the shape memory and subsequently exhibits super-elasticity under the body temperature of the living body to continue supporting the inner wall of the blood vessel.

Since the shape memory alloy has extremely high tenacity, such that it exerts an extremely large mechanical pressure to a portion of the inner wall of the blood vessel, thus possibly damaging the blood vessel. Moreover, there are occasions wherein the stent formed of a shape memory alloy is not uniformly expanded in diameter against the inner wall of the blood vessel when implanted in the blood vessel. If a portion of the stent compresses against the inner wall of the blood vessel prematurely to commence to be expanded in diameter, the blood vessel cannot be expanded uniformly. In this case, the portion of the blood vessel, against which a portion of the stent has compressed prematurely, is enlarged excessively in diameter, and hence is likely to be damaged.

The stent formed of metal such as shape memory alloy, once implanted in the vessel, such as blood vessel, is permanently left in the living body unless it is taken out by surgical operations.

DISCLOSURE OF THE INVENTION

It is an object of the present invention to provide a stent for a vessel, such as blood vessel, which is able to keep the vessel in the expanded state reliably without injuring the vessel.

It is another object of the present invention to provide a stent for a vessel which disappears after lapse of a pre-set period after implantation in the vessel to eliminate the necessity of executing a surgical operation of taking out the stent from the vessel after restoration of the site of lesion.

It is another object of the present invention to provide a stent for a vessel which is able to support the vessel, such as blood vessel, with a uniform force.

It is yet another object of the present invention to provide a stent for a vessel which can be inserted into a meandering vessel, such as blood vessel, with good trackability, and which can be easily and reliably implanted in the targeted site in the vessel.

For accomplishing the above object, the present invention provides a stent for a vessel implanted in the vessel of the living body including a main body portion of the stent formed into a tube by a yarn formed of a biodegradable polymer exhibiting a shape memory function. The main body portion of the stent is shape-memorized to a size that can be retained in the vessel. The main body portion of the stent is implanted in the vessel of the living body as it is contracted in diameter by an external force, and is enlarged in diameter by being heated with the body temperature of the living body.

The yarn used is a concatenated continuous monofilament yarn or a multi-filament yarn made up of a plurality of monofilament yarns unified together.

The main body portion of the stent is formed by the yarn formed of a biodegradable polymer being wound to a tube as the yarn is bent in a zigzag design and is enlarged or contracted in diameter with the bends of the yarn as displacing portions.

In the main body portion of the stent, at least part of neighbouring bends of the yarns wound to a tube as the yarns are bent in a zigzag design are connected to one another so that a pre-set tubular shape of the main body portion of the stent is positively maintained on contracting or enlarging its diameter.

The tubular main body portion of the stent is formed by arraying plural yarns each connected to form a ring as each yarn is bent in a zigzag design, these yarns being juxtaposed along the axial direction of the main body portion of the stent to form a tube.

Each yarn making up the main body portion of the stent is formed of a biodegradable polymer having the glass transition temperature lower than approximately 70° C. Thus, the main body portion of the stent is enlarged in diameter to its shape-memorized state at a temperature close to the body temperature.

Each yarn making up the main body portion of the stent is formed of a biodegradable polymer compounded from one or more of polylactic acid (PLLA), polyglycolic acid (PGA), a copolymer of polyglycolic acid and polylactic acid, polydioxanone, a copolymer of trimethylene carbonate and glycolid, and a copolymer of polyglycolic acid or polylactic acid and ε-caprolactone.

If a radiopaque medium is mixed into or deposited on the yarn, the state of implantation of the stent in the vessel can be easily checked from outside the living body using X-rays.

If antithrombotic drugs or drugs for suppressing neointimal formation are mixed into or deposited on the yarn formed by the biodegradable polymer, these drugs can be administered in a sustained fashion as the stent is dissolved.

Moreover, if a radiation source radiating β-rays or a radiation source radiating γ-rays is mixed into or deposited on the yarn formed of the biodegradable polymer, these rays can be radiated to the lesion as the stent is inserted into the living body, thus assuring sustained irradiation of radiation rays.

Other objects and advantages of the present invention will become apparent from the following description which is made with reference to the accompanying drawings.

BEST MODE FOR CARRYING OUT THE INVENTION

Figure 1:
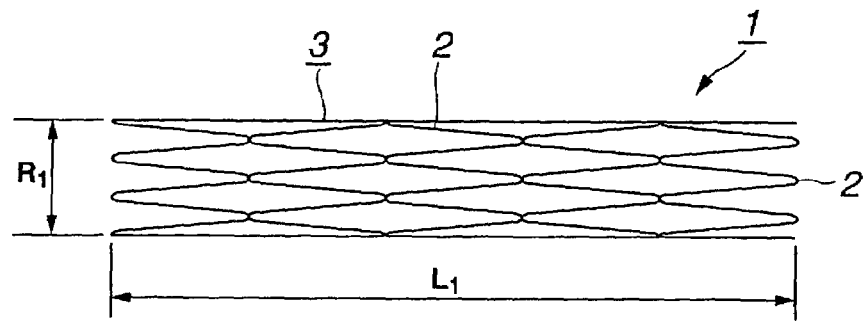
FIG. 1 is a plan view showing a stent for the vessel according to the present invention.

Referring to the drawings, a stent 1 for the vessel according to the present invention is explained in detail.

The stent 1 for the vessel according to the present invention is used as it is inserted into the blood vessel such as coronary artery of a living body and includes a tubular main body portion 3 of the stent comprised of a yarn 2 of a biodegradable polymer having the shape memory function, as shown in FIG. 1.

The yarn 2 is formed of a biodegradable polymer which does not affect the living body when the yarn is implanted in a living body, such as a human body. As this biodegradable polymer, polylactic acid (PLLA), polyglicolic acid (PGA), polyglactin (copolymer of polyglycolic acid and polylactic acid), polydioxanone, polygliconate (copolymer of trimethylene carbonate and glicolid), or a copolymer of polyglicolic acid or polylactic acid and ε-csaprolactone. It is also possible to use a biodegradable polymer obtained on compounding two or more of these materials.

The yarn 2 of the biodegradable polymer may be formed using a screw extruder. For forming the yarn 2 using the screw extruder, pellets formed of a biodegradable polymer as a starting material are heated at a temperature lower than the melting point Tm and dried in vacua. The pellets are charged into a hopper of the screw extruder and melted under compression and heating to a temperature in the vicinity of the melting point Tm or a temperature higher than the melting point and lower than the thermal decomposition point. This melted biodegradable polymer is extruded from a nozzle set at a temperature lower than the melting point Tm and higher than the glass transition temperature (Tg). This extruded biodegradable polymer is rolled up to form a linear member which then is further drawn to form the yarn 2 employed in the present invention.

Figure 2:
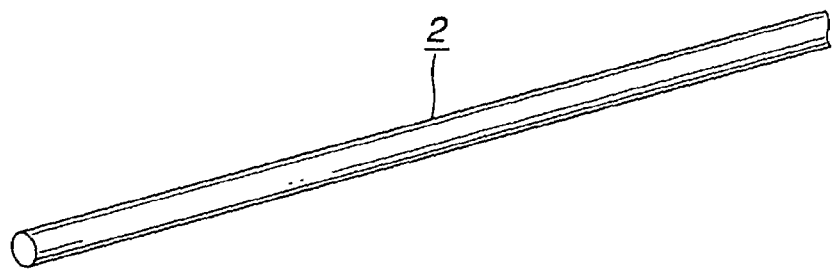
FIG. 2 is a perspective view showing a yarn constituting the stent according to the present invention.

The yarn 2 thus formed is a monofilament comprised of a concatenation of the biodegradable polymer, as shown in FIG. 2.

Figure 3:
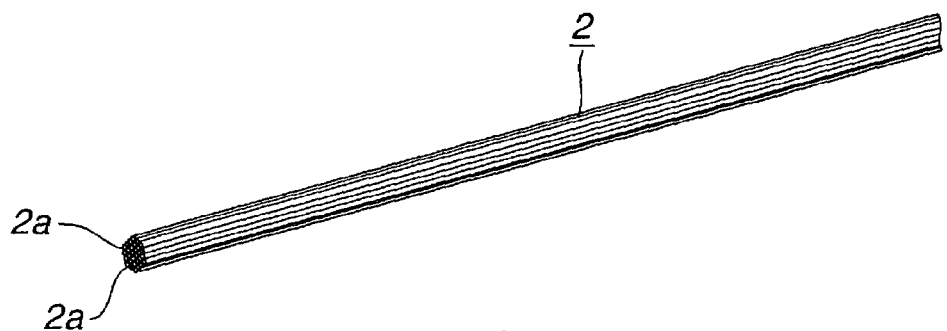
FIG. 3 is a perspective view showing another yarn constituting the stent according to the present invention.

The yarn 2 employed in the present invention may not only be the monofilament but a multifilament yarn comprised of plural monofilaments 2a, as shown in FIG. 3.

The yarn 2 formed by the aforementioned screw extruder using the biodegradable polymer as explained above, is composed of cross-linked polymer molecules and exhibits shape memory properties.

The yarn 2 employed in the present invention may not only be of a circular cross-section but also of a flat cross-section.

Figure 4:
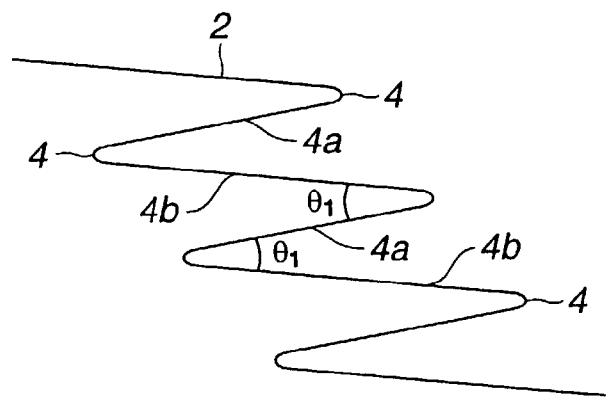
FIG. 4 is a plan view showing the bent state of the yarn constituting a main body portion of the stent.
Figure 5:
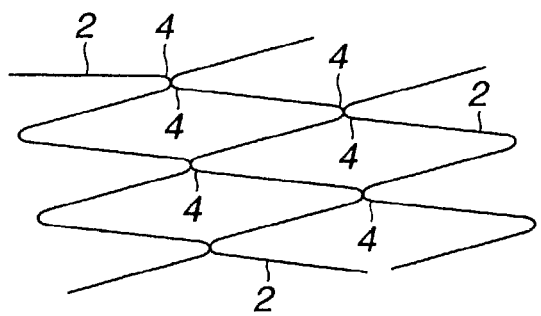
FIG. 5 is an enlarged plan view showing a portion of the main body portion of the stent.
Figure 6:
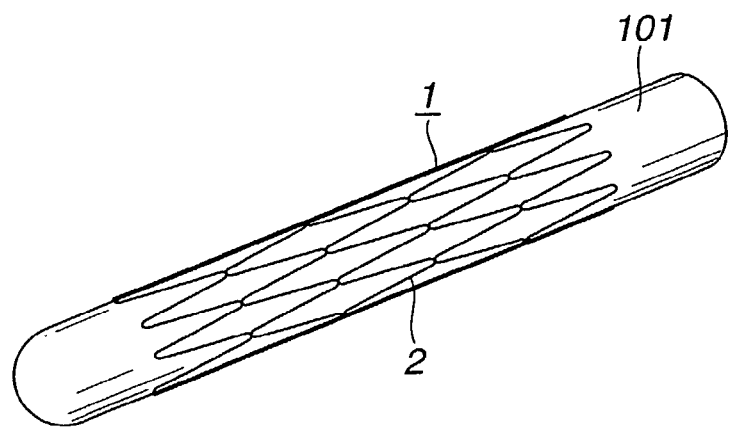
FIG. 6 is a perspective view showing the state of how shape memory is afforded to the stent for the vessel.

The yarn 2, formed as explained above, is bent in a zig-zag design in concatenated vee shapes and wound spirally to constitute a tubular main body portion of the stent 3 as shown in FIG. 4. A spirally wound shape of the yarn 2 is obtained with a side of a bend 4 of the vee shape as a short portion 4a and with its opposite side as a long portion 4b. By setting the lengths of the short portion 4a and the long portion 4b between the bends 4 so as to be approximately equal to each other, the apices of the neighbouring bends 4 are contacted with each other, as shown in FIG. 5. Part or all of the apices of the contacted bends 4 are bonded to one another. The yarn 2 of the main body portion of the stent 3 is positively maintained in the state of keeping the tubular shape by bonding the apices of the bends 4 contacting with each other.

The bends 4 having the apices contacting with each other are bonded together by melting and fusing the contact portions together on heating the contact portions to a temperature higher than the melting point Tm.

The stent 1, constituted using the tubular main body portion of the stent 3, is shape-memorized to the size with which it is implanted in the blood vessel. For realizing this shape memory, the stent 1 is equipped on a shaft-like mold frame 101 sized to maintain the size of the stent 1 implanted in the vessel of the living body, and is heated to a temperature higher than the glass transition temperature (Tg) and lower than the melting point of the biodegradable polymer constituting the yarn 2, so as to be deformed to a size consistent with the size of the mold frame 101. The stent 1 equipped on the mold frame 101 then is cooled, along with the mold frame 101, to a temperature lower than the glass transition temperature (Tg). This affords to the stent 1 the shape memory properties so that the stent is fixed in the deformed state.

The heating for deforming the stent 1 to afford shape memory thereto is achieved by a heating oven.

The stent 1, obtained in this manner, is shape-memorized to the diameter R1 of approximately 3 to 5 mm and to the length L1 of 10 to 15 mm, as shown in FIG. 1. This size corresponds to or is larger than the diameter with which the stent is implanted in the blood vessel of the living body.

Figure 7:
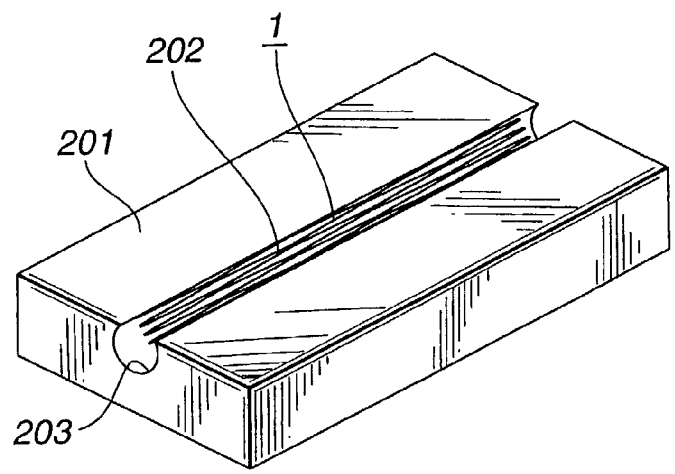
FIG. 7 is a perspective view showing the state of diameter contraction of a stent for vessel in shape memory to the diameter expanded state.

The stent 1 equipped and shape-memorized on the mold frame 101 is contracted in diameter after it is dismounted from the mold frame 101. This contraction in diameter occurs as the main body portion of the stent 3 is deformed under a mechanical force applied from the outer perimeter of the main body portion of the stent 3 in the state in which the stent is cooled to a temperature lower than the glass transition temperature (Tg). The diameter contraction of the stent 1 is realized by thrusting the main body portion of the stent 3 into a diameter-contracting groove 202 provided in a diameter-contracting mold frame 201 as shown in FIG. 7. This diameter-contracting groove 202 is formed as a recessed groove in the major surface of the diameter-contracting mold frame 201 to permit facilitated insertion of the elongated stent 1.

Figure 8:
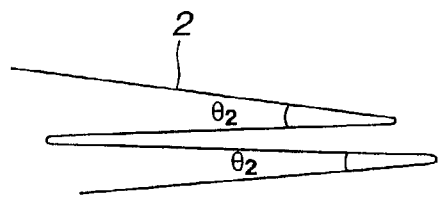
FIG. 8 is a plan view showing the bent state of the yarn when the stent for vessel is contracted in diameter.
Figure 9:
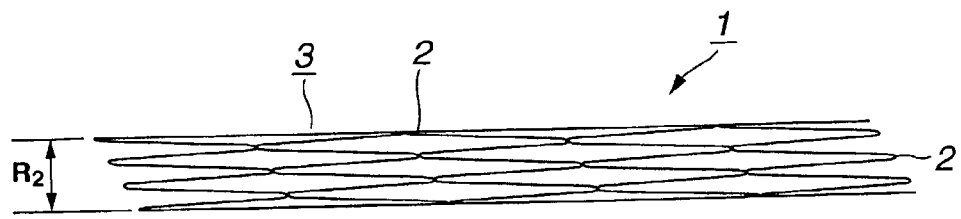
FIG. 9 is a plan view of the stent for vessel showing its diameter-contracted state.

The stent 1, thus pushed into the inside of the diameter-contracting groove 202, is contracted in diameter by displacing the bends 4 so that the opening angle θ1 of the bend 4 will be a smaller opening angle θ2, as shown in FIG. 8. This diameter contraction, achieved by displacing the bends 4, is by deforming the bends 4 of the yarn 2 cooled to a temperature lower than the glass transition temperature (Tg). For example, in the stent 1, shape-memorized to the diameter R1 of approximately 3 to 5 mm, the diameter is reduced to a diameter R2 of approximately 1 to 2 mm, as shown in FIG. 9.

By this diameter contraction, the stent 1, shape-memorized to the diameter-expanded state, is slightly elongated in the longitudinal direction from the shape-memorized state.

The stent 1, pushed into the diameter-contracting groove 202 provided in the diameter-contracting mold frame 201, and thereby contracted in diameter, is pulled out from an opened end 203 of the diameter-contracting groove 202. The stent 1, produced from the yarn 2 formed of the biodegradable polymer, is kept after dismounting from the diameter-contracting mold frame 201 at a temperature lower than the glass transition temperature (Tg) to maintain the strain afforded to the bends 4 representing the displacement portions to keep the diameter-contracted state.

For contracting the diameter of the stent 1, shape-memorized to the diameter-enlarged state, it is possible to use a variety of different methods other than the above-described method of employing the diameter-contracting mold frame 201. For example, the stent 1 may be contracted in diameter by applying a mechanical force from the outer perimeter of the shape-memorized stent 1 without using mold frames.

If the stent 1, contracted in diameter by application of an external force, is heated to a temperature higher than the glass transition temperature (Tg), it is relieved of the strain afforded to the bends 4, so that the bend 4 folded to the small opening angle θ2 is opened to the opening angle θ1 to restore to its original shape-memorized size. That is, the stent 1 on being re-heated to a temperature higher than the glass transition temperature (Tg) is enlarged to its original shape-memorized size, as shown in FIG. 1.

Meanwhile, the stent 1 for the vessel, according to the present invention, is used as it is inserted into the blood vessel, such as the coronary vessel of the living body, and is enlarged in diameter to the shape-memorized state, when inserted into the blood vessel, to support its inner wall. It is noted that the yarn 2, making up the main body portion of the stent 3 of the stent 1 for the vessel, is formed of a biodegradable polymer, with the glass transition temperature (Tg) lower than 70° C., in order to restore to its original shape by the temperature equal or close to body temperature of the living body.

The stent 1, formed by the yarn 2, which has the glass transition temperature (Tg) lower than 70° C. and which is able to restore to its original shape by the body temperature of the living body, can be heated at a temperature not producing heat damages to the blood vessel of the living body, even if it is heated for enlarging its diameter to its shape-memorized state.

The stent 1, implanted on the blood vessel in the diameter-contracted state, is enlarged in diameter to realize the size capable of contacting with the inner wall of the blood vessel by a balloon provided on a catheter. On diameter expansion into contact with inner wall of the blood vessel by the balloon, the stent 1 can be evenly contacted with the inner wall of the blood vessel and heated evenly by the body temperature to restore to its original shape.

If the heated contrast medium is injected into the balloon through a catheter to restore the stent 1 to its original shape, the heating temperature of approximately 50° C. suffices, thus not producing heat damages to the blood vessel.

The temperature dependency in shape restoration of the stent 1 formed by the yarn 2 of polylactic acid (PLLA) with the glass transition temperature (Tg) of approximately 57° C., and the stent 1 formed by the yarn 2 of polyglycolic acid (PGA) with the glass transition temperature (Tg) of approximately 37° C. was indicated.

The yarn 2 was produced as a drawn monofilament, with a diameter of 50 to 300 μm, using the above-described screw extruder, from polylactic acid (PLLA) and polyglycolic acid (PGA). Using this yarn 2, each stent 1 is formed by bending in a zigzag design as explained above and is wound to a tube with a diameter R1 of 4 mm by shape memory action. The tube thus produced was then contracted to the diameter R2 of 1.4 mm. Each stent 1 in the shape-memorized state is of a length L1 of 12 mm.

Figure 10:
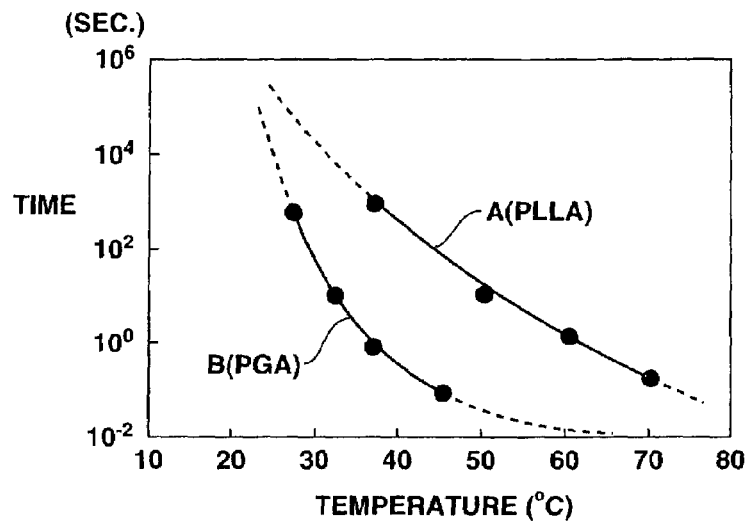
FIG. 10 is a graph showing temperature characteristics of the stent for vessel according to the present invention.

The stent 1, formed by the yarn 2 of polylactic acid PLLA, restores to its original shape at 70° C. in only 0.2 sec, as shown at A in FIG. 10, while recovering its shape at 50° C. in 13 sec and moderately recovering its shape at 37° C. close to the body temperature over approximately 20 minutes. At 20° C. or less, close to the room temperature, the stent 1 is kept in the diameter-contracted state without recovering the shape.

Thus, with the stent 1, formed from the yarn 2 of polylactic acid PLLA, the time needed in shape restoration can be controlled by controlling the heating temperature. Therefore, the rate of shape restoration can be controlled in keeping with the state of the blood vessel in which is implanted the stent 1.

On the other hand, the stent 1, formed from the yarn 2 of polyglycolic acid (PGA), restores to its original shape at 45° C. in only 0.5 second, as shown at B in FIG. 10, while restoring to its original shape in about a second at 37° C. close to the body temperature and in 10 seconds at 30° C. lower than the body temperature. At 15° C. or less, close to room temperature, the diameter-contracted state is maintained without shape recovery.

The stent 1 formed by the yarn 2 of polyglycolic acid (PGA), having a low glass transition temperature (Tg), restores to its original shape rapidly by body temperature on insertion into the blood vessel. Thus, the stent 1 can be applied with advantage to such application in which the stent needs to be enlarged in diameter as soon as it is inserted into the blood vessel. Moreover, since the stent can recover to its original shape promptly with the body temperature without heating, heat control for shape restoration of the stent 1 is facilitated.

Figure 11:
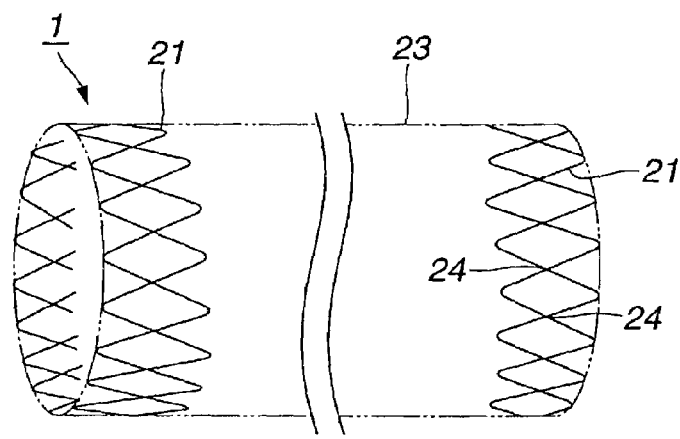
FIG. 11 is a perspective view showing another embodiment of the stent for vessel according to the present invention.

In the stent for vessel 1, described above, the sole yarn 2, bent in a zigzag design for forming bends partway, is wound spirally to form a tubular main body portion of the stent 3. Alternatively, a sole yarn, bent in a zigzag design for forming bends partway, may be formed into a ring, and a plurality of these yarns 21, wound into rings, may then be arrayed side-by-side along the axial direction to form a tubular main body portion of the stent 23, as shown in FIG. 11.

With this main body portion of the stent 23, the apex portions of the bends 24 of the respective juxtaposed yarns 21, contacting with each other, are bonded together to maintain the tubular shape reliably.

The stent 1, comprised of the main body portion of the stent 23, is equipped on the shaft-like mold frame 101, as in the case of the stent 1 described above. The stent 1 of the present embodiment is again heated to a temperature higher than the glass transition temperature (Tg) of the biodegradable polymer constituting the yarn 21 and lower than the melting point Tm, and is shape-memorized to a size with which the stent was implanted in the vessel of the living body. The stent then is contracted to a diameter by e.g., a diameter-contracting mold frame 201, which will allow the stent to be easily introduced into the vessel of the living body.

It suffices if the stent 1 of the present invention is formed as the yarn 2 is bent in a zigzag design to a tube. A variety of methods may be used for winding the yarn in this manner.

Meanwhile, the shape memory restoring force of the shape memory alloy used in a conventionally proposed stent is roughly tens of kilograms (kg)/mm$^2$, whereas that of the biodegradable polymer constituting the yarn of the stent according to the present invention is roughly several kg/mm$^2$. That is, the biodegradable polymer having the shape memory function has a shape memory restoring rest which is appreciably lower than that of the shape memory alloy. Moreover, the rate of recovery to the shape-memorized state of the biodegradable polymer having the shape memory function can be ten times that of the shape memory alloy. The stent formed using the yarn of the biodegradable polymer having the shape memory function having these characteristics can be restored to its original shape memorized state in a time interval not less than 10 times for the stent formed of the shape memory alloy.

Thus, the stent formed of the yarn of the biodegradable polymer having such characteristics that the shape memory restoring force is small and the time of restoration to the shape memorized state is long, is enlarged in diameter evenly without abrupt increase in diameter, if the stent in the contracted-diameter state is inserted into the blood vessel and subsequently enlarged in diameter. Moreover, there is no risk of excessive mechanical pressure being applied to the inner wall of the blood vessel, thus positively preventing the possibility of damaging the blood vessel.

On the other hand, the yarn formed of the biodegradable polymer having the shape memory function has a coefficient of friction smaller than that of the linear member formed of metal, such as shape memory alloy, so that, if the stent is abutted against a portion of the inner wall of the blood vessel during the time the stent is increased in diameter, it slips and expands uniformly on the inner wall surface of the blood vessel without inflicting damages to the blood vessel.

It has been clinically demonstrated that, although a stent used for preventing restenosis of the blood vessel retains its shape for several weeks to several months after it is implanted in the blood vessel, it desirably disappears in several months after implantation.

Since the stent according to the present invention is formed by the yarn of a biodegradable polymer, it retains its shape for several weeks to several months after it is implanted in the blood vessel of a living body, however, it is absorbed into the living tissue to vanish in several months after it is implanted in the blood vessel.

A variety of drugs may be mixed into the yarn of the polymer fibers. If radiopaque agent is mixed at the time of spinning the yarn, the status of the stent for the vessel can be observed with X-rays, so that thrombolytic drug or antithrombotic drug, such as heparin, urokinase or t-PA may be mixed into the yarn to prevent thrombotic restenosis of the blood vessel. Moreover, drugs can be continuously administered. If a radiation source radiating β- or γ-rays is mixed into or coated on the yarn, the lesion site in the living body can be illuminated by the radiations in a sustained and concentrated fashion.

Moreover, by admixing drugs aimed at suppressing the neo intimal hyperplasia on the yarn, it is possible to administer drugs aimed at suppressing the neointimal formation in a sustained fashion.

It is noted that the radiopaque agent, thrombolytic drug or antithrombotic drug, pharmaceuticals aimed at suppressing the neointimal formation, or the radiation source, may also be coated on the surface of the spun yarn.

Figure 12:
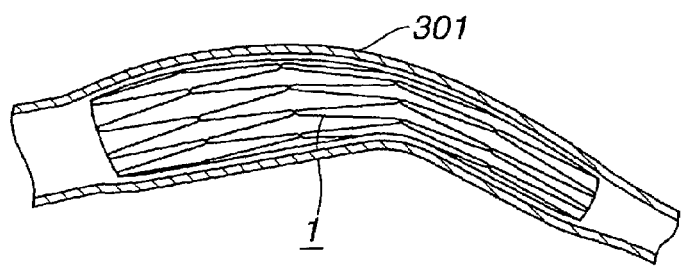
FIG. 12 is a side view showing the state in which the stent for vessel according to the present invention is inserted into the blood vessel.

The stent 1 according to the present invention is constituted by winding the biodegradable polymer yarns, having the shape memory function, in a tube without overlapping, while it can be flexed and deformed easily in the longitudinally, as shown in FIG. 12, and hence can be inserted with good trackability into a bent blood vessel 301, because the stent 1 is formed by winding the yarns of the biodegradable polymer having the shape memory function into a tube without the yarns overlapping with one another. In particular, the stent 1, formed using a yarn having bends partway, can be easily deformed in the longitudinal direction and hence can be introduced into the bent blood vessel 301 with high trackability.

On the other hand, the stent 1 of the present invention is formed without producing overlapping portions of the yarns 2, and can be displaced in the shape-memorized state with the bends 4 of the yarns 2 as the displacing portions. Therefore, the stent 1 can restore its shape smoothly without encountering the resistance by the overlapped yarns 2.

In addition, in the stent 1 of the present invention, in which the yarns 2 are wound without forming overlapping portions, there is no superposed yarn to reduce the damages otherwise inflicted to the wall of the blood vessel.

INDUSTRIAL APPLICABILITY

Since the stent for vessel according to the present invention is constituted using a biodegradable polymer having the shape memory function, the stent can memorize its shape to a size with which it is implanted in the vessel, so that the vessel can be positively maintained in the expanded state without being damaged.

Also, the stent can be easily enlarged in diameter after it is implanted in the vessel, such as blood vessel, and also can support the vessel, such as blood vessel, with an even force, so that there may be provided a stent for vessel that is able to hold the vessel in a stabilized state in a reliably diameter-enlarged state.

In particular, since the stent for vessel according to the present invention is formed using a biodegradable polymer, it can retain its shape for several weeks to several months after it is implanted in the blood vessel, however, the stent can vanish in several months after it is implanted. Thus, the stent may be provided which is clinically most desirable.

The invention claimed is:

1. A method for manufacturing a yarn for a vessel stent comprising the steps of:
   compressing and melting pellets formed of a biodegradable polymer,
   heating said pellets to a temperature in the vicinity of its melting point (Tm) or a temperature higher than its melting point and lower than its thermal decomposition point by a screw extruder,
   extruding said melted biodegradable polymer from a nozzle of said screw extruder to form a yarn, and
   bending said yarn in a zig zag design to constitute a tubular main body portion of said vessel stent to obtain said yarn for the vessel stent,
   said nozzle being controlled to have a temperature not higher than the melting point and not lower than the glass transition temperature of the biodegradable polymer.

2. A method for manufacturing a yarn for a vessel stent according to claim 1 wherein said nozzle is controlled to have the temperature higher than the glass transition temperature (Tg) of said biodegradable polymer.

3. A method for manufacturing a yarn for a vessel stent according to claim 1 wherein said pellets formed of the biodegradable polymer are heated at a temperature lower than its melting point (Tm) under drying in vacuum and then charged into the screw extruder.

4. A method for manufacturing a yarn for a vessel stent according to claim 1 wherein said yarn extruded from the screw extruder is drawn further.

5. A method for manufacturing a yarn for a vessel stent according to claim 1 wherein said yarn extruded from the screw extruder is formed into a non-interrupted continuous monofilament.

6. A method for manufacturing a yarn for a vessel stent according to claim 1 wherein said biodegradable polymer has the glass transition temperature (Tg) lower than approximately 70° C.

7. A method for manufacturing a yarn for a vessel stent according to claim 1 wherein said biodegradable polymers are one or more from among polylactic acid (PLLA), polyglycolic acid (PGA), a copolymer of polyglycolic acid and polylactic acid, polydioxanone, a copolymer of trimethylene carbonate and glycollide, and a copolymer of polyglycolic acid or polylactic acid and ε-caprolactone.

8. A method for manufacturing a yarn for a vessel stent according to claim 1 wherein said biodegradable polymer matrix contains one or more of an X-ray non-transmitting agent, an anti-thrombotic agent, pharmaceuticals for suppressing neointima hyperplasia, a β-ray radiation source and a γ-ray radiation source.

9. A method for manufacturing a yarn for a vessel stent according to claim 1 further comprising a step of depositing one or more of an X-ray non-transmitting agent, an anti-thrombotic agent, pharmaceuticals for suppressing neointima hyperplasia, a β-ray radiation source and a γ-ray radiation source on the surface of said yarn.

10. A method for manufacturing a yarn for a vessel stent comprising the steps of:
    (A) obtaining a yarn made by the following process:
        (1) compressing and melting pellets formed of a biodegradable polymer,
        (2) heating said pellets to a temperature in the vicinity of its melting point (Tm) or a temperature higher than its melting point and lower than its thermal decomposition point by a screw extruder, and
        (3) extruding said melted biodegradable polymer from a nozzle of said screw extruder to form said yarn, and
    (B) bending said yarn in a zig zag design to constitute a tubular main body portion of
        said vessel stent to obtain said yarn for a vessel stent, said nozzle being controlled to have a temperature not higher than the melting point and not lower than the glass transition temperature of the biodegradable polymer.

11. A method for manufacturing a yarn for a vessel stent according to claim 10 wherein said nozzle is controlled to have the temperature higher than the glass transition temperature (Tg) of said biodegradable polymer.

12. A method for manufacturing a yarn for a vessel stent according to claim 10 wherein said pellets formed of the biodegradable polymer are heated at a temperature lower than its melting point (Tm) under drying in vacuum and then charged into the screw extruder.

13. A method for manufacturing a yarn for a vessel stent according to claim 10 wherein said yarn extruded from the screw extruder is drawn further.

14. A method for manufacturing a yarn for a vessel stent according to claim 10 wherein said yarn extruded from the screw extruder is formed into a non-interrupted continuous monofilament.

15. A method for manufacturing a yarn for a vessel stent according to claim 10 wherein said biodegradable polymer has the glass transition temperature (Tg) lower than approximately 70° C.

16. A method for manufacturing a yarn for a vessel stent according to claim 10 wherein said biodegradable polymers are one or more from among polylactic acid (PLLA), polyglycolic acid (PGA), a copolymer of polyglycolic acid and polylactic acid, polydioxanone, a copolymer of trimethylene carbonate and glycollide, and a copolymer of polyglycolic acid or polylactic acid and ε-caprolactone.

17. A method for manufacturing a yarn for a vessel stent according to claim 10 wherein said biodegradable polymer matrix contains one or more of an X-ray non-transmitting agent, an anti-thrombotic agent, pharmaceuticals for suppressing neointima hyperplasia, a β-ray radiation source and a γ-ray radiation source.

18. A method for manufacturing a yarn for a vessel stent according to claim 10 further comprising a step of depositing one or more of an X-ray non-transmitting agent, an anti-thrombotic agent, pharmaceuticals for suppressing neointima hyperplasia, a β-ray radiation source and a γ-ray radiation source on the surface of said yarn.

* * * * *